(12) United States Patent
Eu et al.

(10) Patent No.: US 8,981,120 B2
(45) Date of Patent: Mar. 17, 2015

(54) ORGANIC SEMICONDUCTOR

(71) Applicants: JX Nippon Oil & Energy Corporation, Chiyoda-ku (JP); Kyoto University, Kyoto-shi (JP)

(72) Inventors: Seunghun Eu, Chiyoda-ku (JP); Tsuyoshi Asano, Chiyoda-ku (JP); Kazuo Akagi, Kyoto (JP)

(73) Assignees: JX Nippon Oil & Energy Corporation, Chiyoda-Ku, Tokyo (JP); Kyoto University, Kyoto-Shi, Kyoto (JP)

( * ) Notice: Subject to any disclaimer, the term of this patent is extended or adjusted under 35 U.S.C. 154(b) by 0 days.

(21) Appl. No.: 14/074,799

(22) Filed: Nov. 8, 2013

(65) Prior Publication Data
US 2014/0114078 A1    Apr. 24, 2014

Related U.S. Application Data

(63) Continuation of application No. PCT/JP2012/002989, filed on May 7, 2012.

(30) Foreign Application Priority Data

May 9, 2011   (JP) ................. 2011-104618

(51) Int. Cl.
*H01L 51/00*      (2006.01)
*C07D 333/18*     (2006.01)

(52) U.S. Cl.
CPC .......... *H01L 51/0036* (2013.01); *C07D 333/18* (2013.01)
USPC .......................................................... 549/59

(58) Field of Classification Search
CPC .................. H01L 51/0036; C07D 333/18
USPC .......................................................... 549/59
See application file for complete search history.

(56) References Cited

U.S. PATENT DOCUMENTS

| 7,183,418 | B2 | 2/2007 | Heeney et al. |
| 2004/0119049 | A1 | 6/2004 | Heeney et al. |
| 2005/0090640 | A1 | 4/2005 | Heeney et al. |
| 2009/0159876 | A1* | 6/2009 | Ohba et al. ............. 257/40 |
| 2010/0084000 | A1 | 4/2010 | Ueda |
| 2010/0304147 | A1 | 12/2010 | Meyer-Friedrichsen et al. |

FOREIGN PATENT DOCUMENTS

| JP | 2000-143777 A | 5/2000 |
| JP | 2004-186695 A | 7/2004 |
| JP | 2005-076030 A | 3/2005 |
| JP | 2008-106239 A | 5/2008 |
| JP | 2011-505681 A | 2/2011 |

OTHER PUBLICATIONS

International Search Report (PCT/ISA/210) mailed on Jun. 12, 2012, by the Japanese Patent Office as the International Searching Authority for International Application No. PCT/JP2012/002989.
International Preliminary Report on Patentability (PCT/IB/373) and Written Opinion of the International Searching Authority (PCT/ISA/237) issued on Nov. 12, 2013, by the Japanese Patent Office as the International Searching Authority in corresponding International Application No. PCT/JP2012/002989, and an English Translation.
Wen-Chang Chen et al., "Small-Bandgap Conducting Polymers Based on Conjugated Poly(Heteroarylene Methines). 2. Systhesis, Structure, and Properties", Macromolecules, 1995, 28, 465-480.
Chen et al.: "Small-Bandgap Conducting Polymers Based on Conjugated Poly(heteroarylene methines). 1. Precursor Poly(heteroarylene methylenes)", Macromolecules, American Chemical Society, US, vol. 28, No. 2, Jan. 16, 1995, pp. 454-464, XP000482549.
Extended European Search Report issued in corresponding European Application No. 12782276.5 on Sep. 22, 2014 (6 pages).

* cited by examiner

*Primary Examiner* — Noble Jarrell
*Assistant Examiner* — John Mauro
(74) *Attorney, Agent, or Firm* — Buchanan Ingersoll & Rooney PC

(57) ABSTRACT

An organic semiconductor represented by the following formula (1).

[Formula 1]

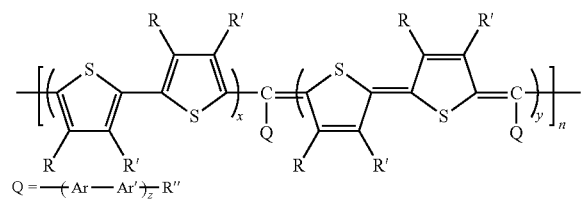

wherein Ar and Ar' are or are not the same as each other and each of them is independently a cyclic compound having a conjugated structure; R and R' are or are not the same as each other and each of them is independently one of a straight chain alkyl group, branched alkyl group, straight chain alkoxy group, branched alkoxy group, hydrogen, and halogen; R" is one of a straight chain alkyl group, branched alkyl group, straight chain alkoxy group, branched alkoxy group, hydrogen, and halogen; x, y, and z are multiples of 0.5, and x≤z, y≤z; and n is a constant of 1 to 1000.

7 Claims, No Drawings

ORGANIC SEMICONDUCTOR

BACKGROUND OF THE INVENTION

1. Field of the Invention

The present invention relates to an organic semiconductor applicable to organic electronic devices, such as an organic thin-film solar cell, organic transistor, photosensor, and electroluminescence device.

2. Description of the Related Art

Organic semiconductors having a charge (electron or hole) transfer characteristic are expected to be applied to organic electronic devices. Because an organic electronic device is rich in flexibility; its area and weight can be expected to be enlarged and reduced, respectively; and a simple and inexpensive manufacturing method can be expected, it is considered to be a promising technique. In manufacturing a high-performance organic electronic device, high charge transfer characteristic is particularly desired. In an organic thin-film solar cell, for example, a larger current can be obtained as the charge transfer characteristic thereof is higher, thereby allowing a solar cell exhibiting a high conversion efficiency to be manufactured. In an organic transistor, for example, a flowing current becomes larger as the charge transfer characteristic thereof is higher, thereby allowing the transistor to exhibit excellent characteristics as a transistor.

As an index for the charge transfer characteristic of an organic semiconductor, charge mobility can be mentioned. The charge mobility represents the moving speed of a charge in a unit electric field. An organic semiconductor having a higher charge mobility is more excellent in a charge transfer characteristic. It is recognized that an improvement in the interaction between π-planes in an organic semiconductor is effective in improving the charge mobility thereof. It is required to extend a π-conjugated system in order to improve the interaction between π-planes. As a typical method of obtaining an extended π-conjugated system, a unit structure having a further large π-plane, such as, for example, naphthalene and anthracene, is introduced into a molecule. Also, it is known that a π-conjugated system is extended by making the electronic structure of a molecule to polarize with a unit structure, having a large difference between the electron-donating property and the electron-attracting property, being introduced into the molecule.

RELATED ART DOCUMENTS

Patent Documents

[Patent Document 1] Japanese Patent Application Publication No. 2005-076030
[Patent Document 2] Japanese Patent Application Publication No. 2008-106239

Non-Patent Document

[Non-Patent Document 1] Macromolecules, 1995, 28, 465

However, there is the problem that, because an organic semiconductor with a high charge transfer characteristic has an extended π-plane and a large π-π interaction between molecules, the solubility in an organic solvent is decreased. When the solubility in an organic solvent is low, it is difficult to manufacture a device by a low-cost process, such as coating, which leads to an increase in manufacturing cost. In addition, an organic semiconductor with low solubility cannot exhibit a high performance in some cases, depending on application fields. For example, in an organic electronic device in which an extended contact area between a P-type (hole transfer) organic semiconductor and an N-type (electron transfer) organic semiconductor is preferred, such as an organic thin-film solar cell, the charge separation efficiency on a P/N interface is decreased, and hence a high short-circuit current density value (Jsc) and a high Fill-factor value cannot be obtained, thereby not allowing a device having a high performance to be manufactured.

On the other hand, there is the concern that an organic electronic device may be deteriorated due to an oxidation reaction of the device caused by air. The oxidation of an organic semiconductor is caused with an electron in a valance band being taken by air. A cation thus generated reacts with another substance present around it, thereby becoming a substance different from the original one. The possibility at which such a reaction is caused can be estimated from the oxidation-reduction potential of an organic semiconductor and those of oxygen and water, and it is known that, the higher the ionization potential of the organic semiconductor, the lower the reactivity thereof. That is, in order to improve the stability of an organic semiconductor, it is desirable to reduce the energy level of a valance band. That is, it is desirable to enhance the ionization potential of the organic semiconductor. In addition, a device having a high performance can also be manufactured by adopting an organic semiconductor having a high ionization potential, depending on application fields. For example, the open circuit voltage (Voc) of an organic thin-film solar cell is determined by the difference between the ionization potential of a P-type organic semiconductor and the electron affinity of an N-type organic semiconductor, and a higher open circuit voltage can be obtained as the difference is larger, thereby allowing an organic thin-film solar cell exhibiting an excellent energy conversion efficiency to be manufactured.

Patent Document 1 discloses a method in which charge mobility is intended to be improved by introducing a quinoid-type resonance structure into a conjugated polymer. Although charge mobility can be improved according to this method, it is difficult to manufacture an organic semiconductor having high charge mobility at a low cost because a reaction using an expensive transition metal is adopted.

Patent Document 2 discloses a method in which the charge mobility of an organic semiconductor is intended to be improved by repeating, in a conjugated polymer, molecules having electron-donating properties different from each other. It is considered that, because polarization of an electron density is caused in a molecule according to this method, solubility may be decreased.

Non-Patent Document 1 discloses a method in which a polymer having a low band gap is polymerized by introducing a quinoid-type resonance structure into a conjugated polymer. However, the ionization potential of the disclosed polymer is low, and charge mobility and solubility in an organic solvent are not described.

SUMMARY OF THE INVENTION

The present invention has been made in view of these situations, and a purpose of the invention is to provide an organic semiconductor that exhibits excellent charge mobility and ionization potential and has high solubility in an organic solvent by which it can be easily formed into a film by coating, etc.

An aspect of the present invention is an organic semiconductor. The organic semiconductor is formed by a repeating unit having a structure represented by the following formula (1) and has an ionization potential higher than 5.0 eV.

[Formula 1]

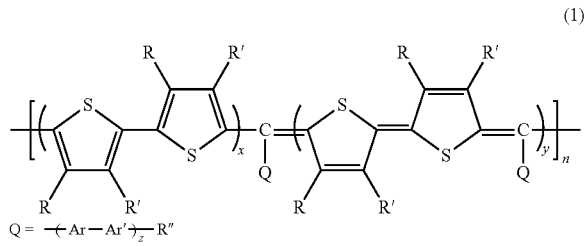

wherein Ar and Ar' are or are not the same as each other and each of them is independently a cyclic compound having a conjugated structure; R and R' are or are not the same as each other and each of them is independently one of a straight chain alkyl group, branched alkyl group, straight chain alkoxy group, branched alkoxy group, hydrogen, and halogen; R" is one of a straight chain alkyl group, branched alkyl group, straight chain alkoxy group, branched alkoxy group, hydrogen, and halogen; x, y, and z are multiples of 0.5, and x≤z, y≤z; and n is a constant of 1 to 1000. Herein, an example of the halogen to be used in R, R', and R" includes, for example, fluorine.

In the above formula (1), each of Ar and Ar' is preferably an arylene group or hetero arylene group each having a substituent group; each of R and R' is preferably one of a straight chain alkyl group, branched alkyl group, hydrogen, and halogen; and R" is preferably one of a straight chain alkoxy group, branched alkoxy group, hydrogen, and halogen.

In the above formula (1), n may be a value of 5 to 1000. The hole mobility of an organic semiconductor according to the aspect may be $3.0 \times 10^{-5}$ cm$^2$/Vs or more, when measured by an SCLC method. The solubility of the organic semiconductor according to the aspect may be 25 mg or more in 1 mL of chlorobenzene.

ADVANTAGE OF THE INVENTION

According to the present invention, it is expected that an organic semiconductor can be provided, the organic semiconductor being applicable to organic electronic devices having excellent performance and stability, such as, for example, an organic transistor, electroluminescense device, photosensor, and organic thin-film solar cell.

DETAILED DESCRIPTION OF THE INVENTION

The invention will now be described by reference to the preferred embodiments. This does not intend to limit the scope of the present invention, but to exemplify the invention.

Hereinafter, an organic semiconductor material according to an embodiment will be described.

(Organic Semiconductor)

An organic semiconductor according to the present embodiment has a repeating unit represented by the following formula (1) and has an ionization potential higher than 5.0 eV. Herein, the ionization potential is a value obtained when the vacuum level of the organic semiconductor is 0 eV. In the formula (1), Ar and Ar' are or are not the same as each other and each of them is independently a cyclic compound having a conjugated structure; R and R' are or are not the same as each other and each of them is independently one of a straight chain alkyl group, branched alkyl group, straight chain alkoxy group, branched alkoxy group, hydrogen, and halogen; R" is one of a straight chain alkyl group, branched alkyl group, straight chain alkoxy group, branched alkoxy group, hydrogen, and halogen; x, y, and z are multiples of 0.5, and x≤z, y≤z; and n is a constant of 1 to 1000.

[Formula 2]

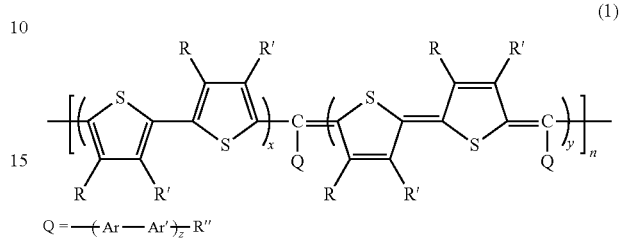

In the above formula (1), each of Ar and Ar' may be an arylene group or hetero arylene group each having a substituent group.

In the above formula (1), each of Ar and Ar' may be benzene having an alkyl substituent group or alkoxy substituent group.

Examples of Ar and Ar' in the above formula (1) will be presented below, but Ar and Ar' should not be limited thereto.

[Formula 3]

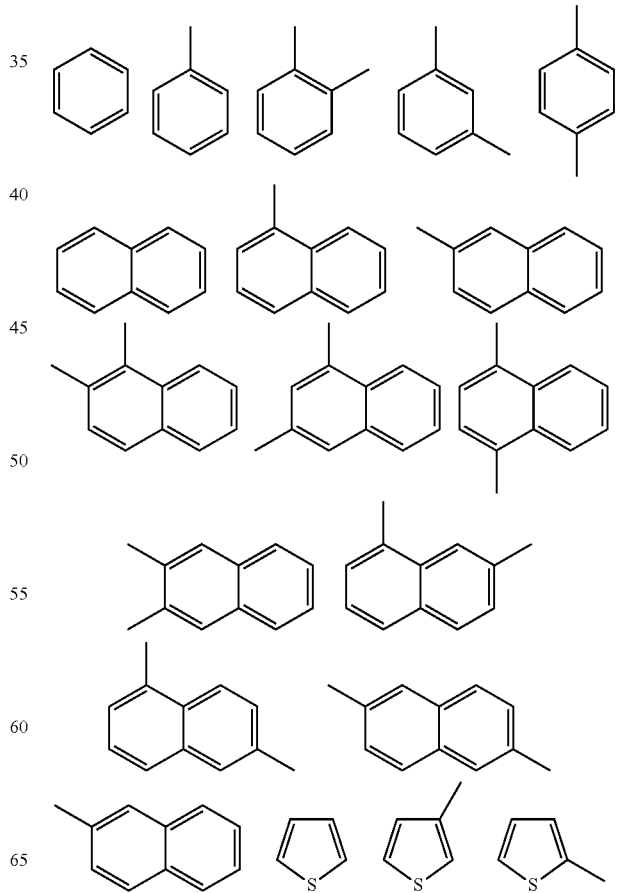

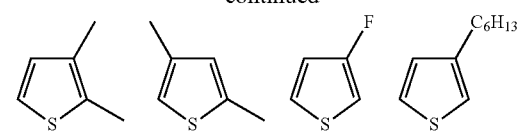

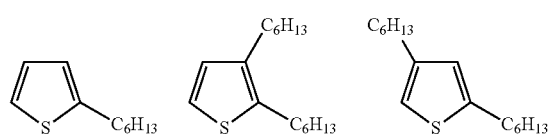

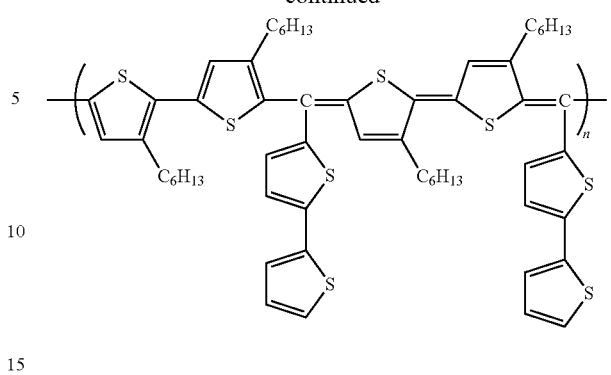

In the above formula (1), R and R' may be one of a straight chain alkyl group, branched alkyl group, hydrogen, or halogen.

In an above chemical formula (1), R" may be one of a straight chain alkoxy group, branched alkoxy group, and halogen. The number of the carbons in a suitable alkoxy group is preferably 1 to 18, and more preferably 5 to 13.

In the above formula (1), it is more preferable that $z \geq 1.5 \times x$ and $z \geq 1.5 \times y$.

In the above formula (1), n is more preferably a constant of 5 to 1000.

The hole mobility of an organic semiconductor represented by the above formula (1) is preferably $3.0 \times 10^{-5}$ cm$^2$/Vs or more, when measured by an SCLC method. The hole mobility is more preferably $6.0 \times 10^{-5}$ cm$^2$/Vs or more, and still more preferably $1.0 \times 10^{-4}$ cm$^2$/Vs or more.

The ionization potential of an organic semiconductor represented by the above formula (1) is more preferably 5.2 eV or higher, and still more preferably 5.4 eV or higher, when the vacuum level of the organic semiconductor is assumed to be 0 eV.

The solubility of an organic semiconductor represented by the above formula (1) is preferably 25 mg or more in 1 mL of chlorobenzene, more preferably 30 mg or more, and still more preferably 35 mg or more.

Embodiments in which the aforementioned respective elements are appropriately combined can also be encompassed within the scope of the invention for which protection is sought by this application. Hereinafter, specific examples of the organic semiconductor will be described, but the organic semiconductor should not be limited thereto.

[Formula 4]

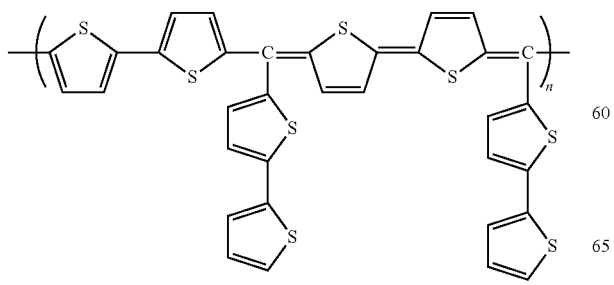

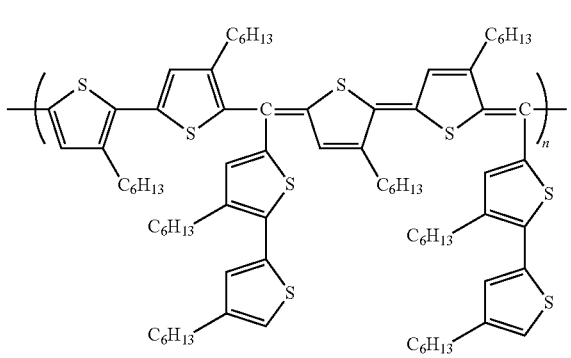

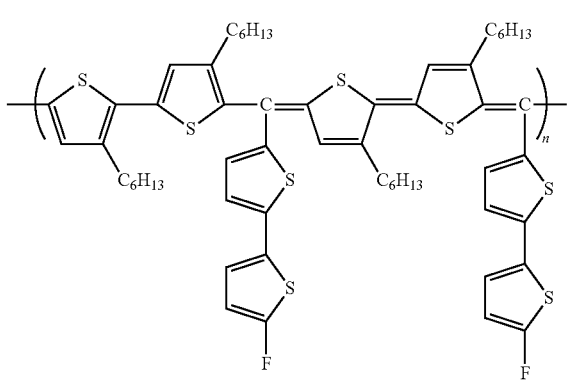

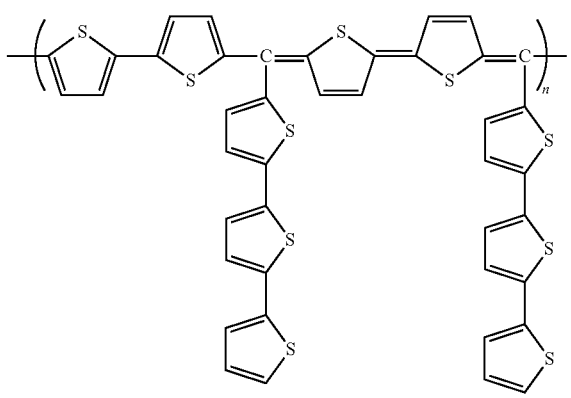

-continued

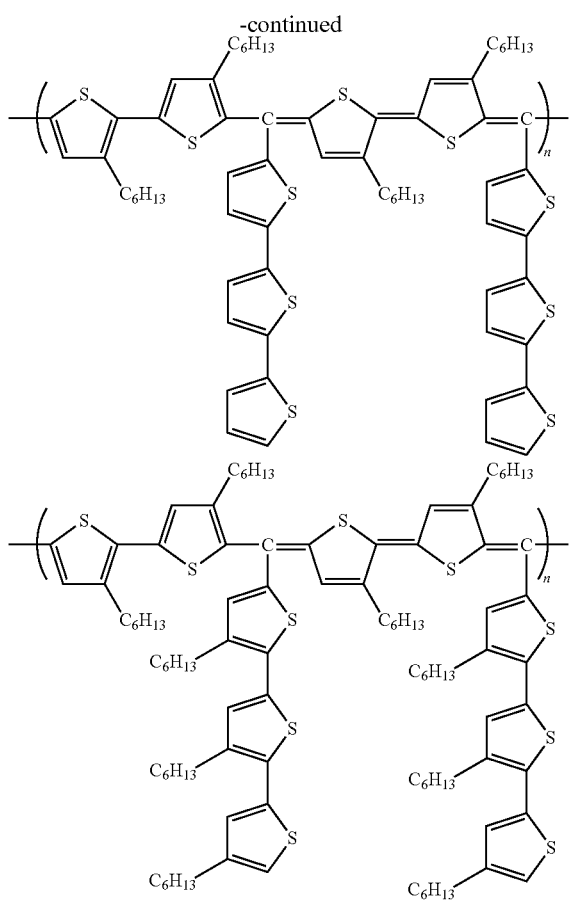

EXAMPLES

Hereinafter, the present invention will be described in detail based on Examples, but the invention should not be limited at all by Examples.

An organic semiconductor of Example 1 is an organic semiconductor P1 represented by the following formula (1-1q).

[Formula 5]

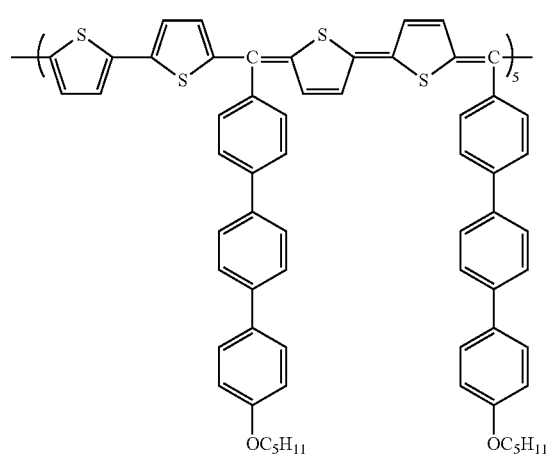

(1-1q)

An organic semiconductor of Comparative Example 1 is an organic semiconductor P2 represented by the following formula (1-2q).

[Formula 6]

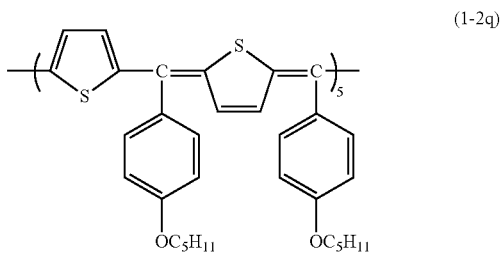

(1-2q)

An organic semiconductor of Comparative Example 2 is an organic semiconductor P3 represented by the following formula (1-3q).

[Formula 7]

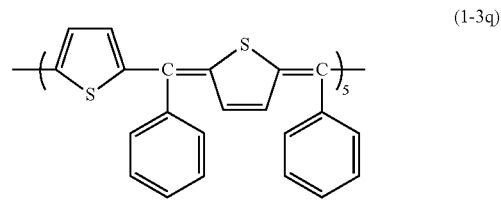

(1-3q)

(Synthesis Process of Organic Semiconductor)

A synthesis process of each of the organic semiconductors used in Example 1 and Comparative Examples 1 and 2 will be described below.

Synthesis of 4-Bromo-4'-pentyloxybiphenyl (A1)

[Formula 8]

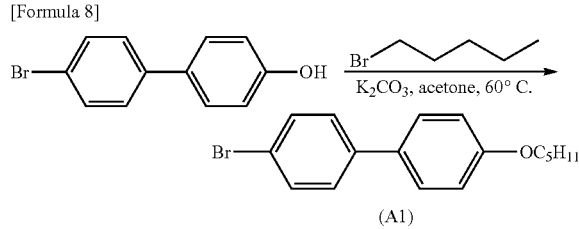

Under an argon atmosphere, 4-bromo-4'-hydroxybiphenyl (3.0 g, 12 mmol), 1-bromopentane (3.6 g, 24 mmol), and potassium carbonate (1.66 g, 12 mmol) were dissolved in acetone (60 mL) and stirred under a reflux condition for 24 hours. After they reacted with each other, liquid separation and extraction were performed with water and chloroform. After an organic layer was dried with anhydrous sodium sulfate and filtered, the solvent was distilled off under a reduced pressure. After the obtained reaction mixture was separated and purified with a silica gel column chromatography using chloroform as a moving bed, the mixture was purified by a recrystallization method using chloroform and hexane. Thereby, a white solid of 4-Bromo-4'-pentyloxybiphenyl (A1) was obtained (1.99 g, yield: 53%). The obtained product (A1) was identified by using a 1H-NMR method.
1H-NMR (CDCl$_3$, 400 MHz) δ=7.53-7.51 (d, 2H), 7.48-7.46 (d, 2H), 7.42-7.40 (d, 2H), 7.00-6.95 (d, 2H), 4.01-3.98 (t, 2H), 1.81 (m, 2H), 1.42 (m, 4H), and 0.94 (t, 3H).

Synthesis of 4"-(pentyloxy)-[1,1':4',1"-terphenyl]-4-carbaldehyde (A2)

[Formula 9]

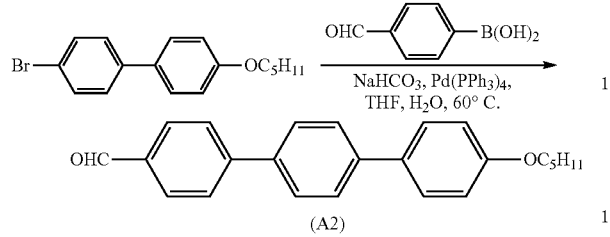

(A2)

Under an argon atmosphere, (4-formylphenyl)boronic acid (0.54 g, 3.6 mmol), 4-Bromo-4'-pentyloxy-biphenyl (0.958 g, 3 mmol) 1) (A1), sodium hydrogen carbonate (0.76 g, 9 mmol), and tetrakis(triphenylphosphine)palladium (Pd (PPh$_3$)$_4$) (0.057 g, 0.030 mmol) were dissolved in THF (15 mL) and water (15 mL) and stirred under a reflux condition. After they reacted with each other, liquid separation and extraction were performed with water and chloroform. After an organic layer was dried with anhydrous sodium sulfate and filtered, the solvent was distilled off under a reduced pressure. After the obtained reaction mixture was separated and purified with a silica gel column chromatography using chloroform as a moving bed, the mixture was purified by a recrystallization method using chloroform and hexane. Thereby, a white solid of 4"-(pentyloxy)-[1,1':4',1"-terphenyl]-4-carbaldehyde (A2) was obtained (0.60 g, yield: 58%). The obtained product (A2) was identified by using a 1H-NMR method. 1H-NMR (CDCl$_3$, 400 MHz) δ=10.06 (s, 1H, CHO), 7.95-7.97 (d, 2H, phenylene), 7.79-7.81 (d, 2H, phenylene), 7.71-7.66 (m, 4H, phenylene), 7.00-6.98 (s, 2H, phenylene), 4.03-3.99 (t, 2H, —O—CH$_2$—), 1.84-1.81 (t, 2H, —CH$_2$—), 1.47-1.40 (m, 4H, —CH$_2$—), and 0.93-0.97 (t, 3H, —CH$_3$). 13C NMR (CDCl$_3$, 100 MHz) δ=191.7, 159.0, 146.7, 141.0, 137.8, 135.2, 132.4, 130.2, 128.0, 127.2, 114.9, 68.1, 29.0, 28.3, 22.7, and 14.1.

Synthesis of 1-1b

[Formula 10]

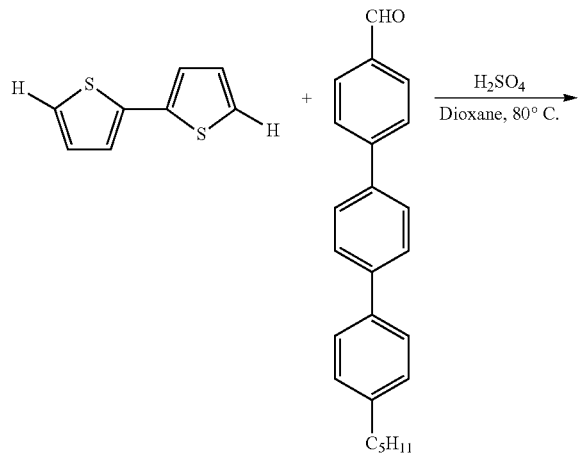

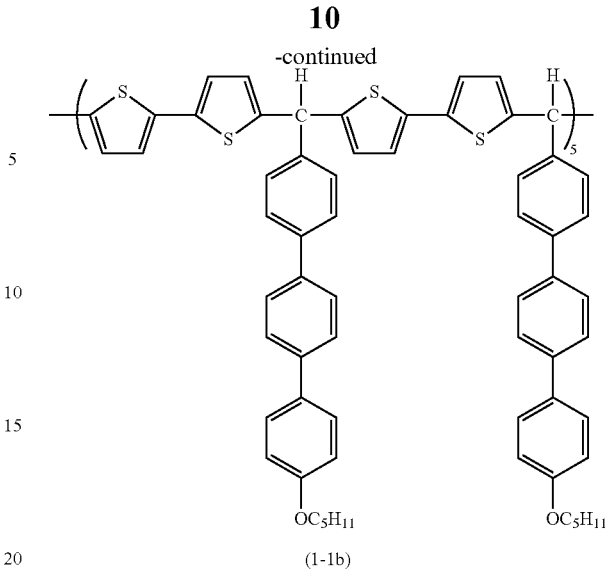

(1-1b)

Under an argon atmosphere, 2,2'-Bithiophene (0.25 g, 1.5 mmol), 4"-(pentyloxy)-[1,1':4',1"-terphenyl]-4-carbaldehyde (0.603 g, 1.75 mmol) (A2) was dissolved in dioxane (4 ml), and concentrated sulfuric acid (0.05 mL (0.5 mmol)) was dropped. Thereafter, the reaction temperature was maintained at 80° C. and the solution was stirred for 24 hours. The compound after the reaction was purified by recrystallization using methanol or acetone to obtain 1-1b having a black color (0.394 g, yield: 34%). The obtained product (1-1b) was identified by using a 1H-NMR method. 1H-NMR (CDCl$_3$, 400 MHz) δ=7.59-7.38 (10H), 6.94 (4H), 6.73 (2H), 5.76 (0.65H), 3.98 (2H), 2.15 (2H), 1.80 (2H), 1.44 (2H), and 0.92 (3H).

Synthesis of Organic Semiconductor 1-1q to be used in Example 1

Organic semiconductor 1-1 to be used in Example 1 was synthesized according to the following reaction formula.

[Formula 11]

(1-1b)

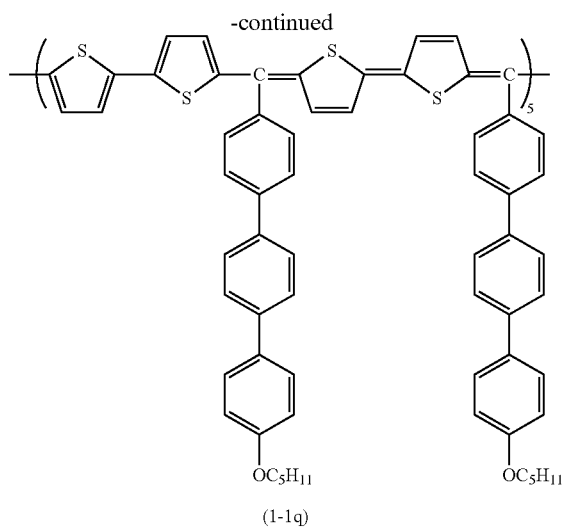

(1-1q)

Under an argon atmosphere, 1-1b (0.025 g) and 2,3-dichloro-5,6-dicyano-1,4-benzoquinone (DDQ) (0.014 g, 0.061 mmol) were dissolved in THF (1 mL) and the solution was stirred at 60° C. for 24 hours. The compound after the reaction was purified by a recrystallization method using methanol or acetone to obtain 1-1q having a reddish black color (0.010 g, yield: 20%). The obtained product (1-1q) was identified by using a 1H-NMR method. 1H NMR (CDCl$_3$, 400 MHz) δ=7.6 (6H), 7.24-7.20 (4H), 6.80-7.00 (6H), 4.0 (2H), 1.90-1.70 (6H), and 0.93 (3H).

Synthesis of Organic Semiconductor 1-2q to be used in Comparative Example 1

Organic semiconductor 1-2q to be used in Comparative Example 1 was synthesized according to the following reaction formula.

[Formula 12]

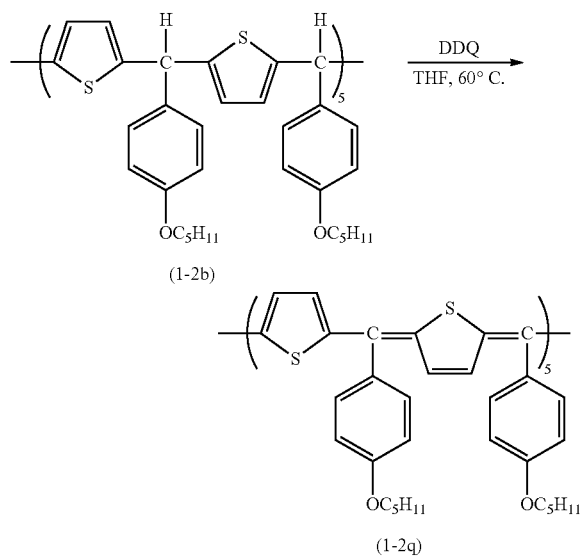

Under an argon atmosphere, 2,2'-Bithiophene (0.30 g, 1.75 mmol) and 4-n-pentyloxybenza-ldehyde (0.403 g, 2.1 mmol) were dissolved in dioxane (6 ml) and concentrated sulfuric acid (0.06 mL (0.6 mmol)) was dropped. Thereafter, the reaction temperature was maintained at 80° C. and the solution was stirred for 24 hours. The compound after the reaction was purified by recrystallization using methanol or acetone to obtain 1-2b having a red color (0.352 g, yield: 50%). Subsequently, 1-2b (0.030 g) and 2,3-dichloro-5,6-dicyano-1,4-benzoquinone (DDQ) (0.016 g, 0.07 mmol) were dissolved in THF (1.5 mL) and the solution was stirred at 60° C. for 24 hours. The compound after the reaction was purified by recrystallization using methanol or acetone to obtain 1-2q having a reddish black color (0.014 g, yield: 47%). The obtained product (1-2q) was identified by using a 1H-NMR method. 1H-NMR (CDCl$_3$, 400 MHz) δ=7.59-7.16 (broad, 14H), 4.10-4.00 (2H), and 1.62-1.26 (9H).

Synthesis of Organic Semiconductor 1-3q to be used in Comparative Example 2

Organic semiconductor 1-3q to be used in Comparative Example 2 was synthesized according to the following reaction formula.

[Formula 13]

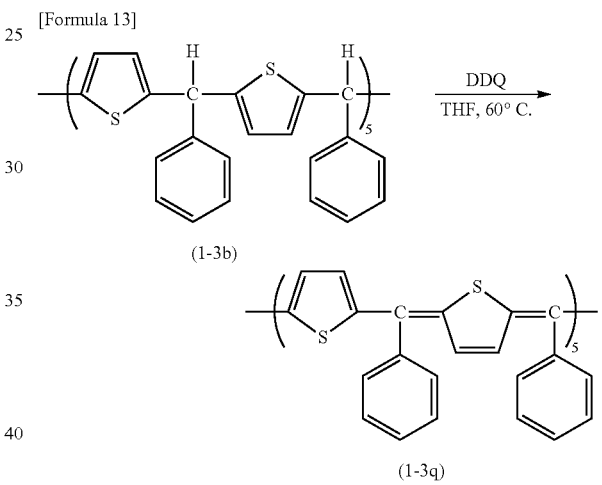

Under an argon atmosphere, 2,2'-Bithiophene (0.5 g, 3 mmol) and benzaldehyde (0.372 g, 3.5 mmol) were dissolved in dioxane (4 ml), and concentrated sulfuric acid (0.1 mL (0.1 mmol)) was dropped. Thereafter, the reaction temperature was maintained at 80° C. and the solution was stirred for 24 hours. The compound after the reaction was purified by recrystallization using methanol or acetone to obtain 1-3b having a red color (0.300 g, yield: 34%). Subsequently, 1-3b (0.030 g) and 2,3-dichloro-5,6-dicyano-1,4-benzoquinone (DDQ) (0.014 g, 0.061 mmol) were dissolved in THF (1 mL) and the solution was stirred at 60° C. for 24 hours. The compound after the reaction was purified by recrystallization using methanol or acetone to obtain 1-3q having a reddish black color (0.010 g, yield: 33%). The obtained product (1-3q) was identified by using a 1H-NMR method. 1H-NMR (CDCl$_3$, 400 MHz) δ=7.52-7.00 (b, 14H, phenyl and thiophene rings).

(Measurement of Hole Mobility)

The hole mobility measured by the SCLC method is a value determined as follows. After commercially available PEDOT:PPS (product name: Starck AI 4083) was formed into a film on an ITO transparent electrode by spin-coating, the film was dried by heating to a temperature of 120 to 150° C. to form a PEDOT:PPS film having a thickness of approximately 40 nm.

A coating liquid was produced by adding a predetermined amount of the organic semiconductor to a chlorobenzene solvent, and the coating liquid was spin-coated on the PEDOT:PPS film. Thereafter, the coated liquid was dried at a predetermined temperature, so that an organic semiconductor having a thickness of approximately 130 nm was formed. A film of Au was formed on the obtained organic semiconductor layer by a vacuum deposition process such that the thickness thereof becomes 100 nm. The film formation speed was adjusted not to exceed 0.01 nm per second. The produced device (ITO transparent electrode/PEDOT:PSS film/photoelectric conversion layer/Au) was put into a black box such that a current (J)-voltage (V) property was measured. After the obtained current-voltage property was log-log plotted with the vertical axis representing $J^{1/2}$ and the horizontal axis representing V, a slope (a) was calculated by fitting the plot in an SCLC region. From the equation of $(J)^{1/2}=\{9\in0\in r\mu/8(L^3)\}^{1/2}V$, the portion of $\{9\in0\in r\mu/8(L^3)\}^{1/2}$ is equal to the slope calculated from the graph, and hence $a=\{9\in0\in r\mu/8(L^3)\}^{1/2}$ holds. This equation was solved with respect to $\mu$, and $\mu=\{8(L^3)(a^2)\}/\{9\in0\in r\}$ was obtained. Then, by substituting $\in0$ and $\in r$ thereinto, (a) was calculated. Herein, $\mu$ is the mobility of the organic semiconductor, L is the thickness of the organic semiconductor, $\in0$ is the dielectric constant of vacuum, and $\in r$ is the dielectric constant of the organic semiconductor.

(Measurement of Ionization Potential)

The ionization potential obtained when the vacuum level of the organic semiconductor is 0 eV is a value measured by using a photoelectron spectroscopy in air (AC-3®, made by RIKEN KEIKI CO., LTD.). A sample by which the ionization potential is evaluated was produced by the following way. A coating liquid was produced by adding a predetermined amount of the polymer to 1 mL of a chlorobenzene solvent under a nitrogen atmosphere, and the coating liquid was spin-coated on a substrate. Thereafter, the coating liquid was dried at a predetermined temperature to form a layer having a thickness of approximately 120 nm.

(Measurement of Solubility)

The solubility is a value determined in the following way. A predetermined amount of the organic semiconductor and 1 mL of chlorobenzene were put into a sample bottle with a lid under a nitrogen atmosphere. The weight, obtained when precipitation was not visually confirmed after the above solution was stirred for 10 minutes and then left uncontrolled for 10 minutes, was determined as the solubility.

(Measurement Results)

The solubility in 1 mL of chlorobenzene, hole mobility, and ionization potential of the organic semiconductor according to each of Example 1 and Comparative Examples 1 and 2 were measured. The results of the measurements are shown in Table 1.

TABLE 1

| | SOLUBILITY IN 1 mL OF CHLOROBENZENE (mg) | HOLE MOBILITY (cm$^2$/Vs) | IONIZATION POTENTIAL (eV) |
|---|---|---|---|
| EXAMPLE 1 | 30 | $3.4 \times 10^{-5}$ | 5.7 |
| COMPARATIVE EXAMPLE 1 | 23 | $5.7 \times 10^{-6}$ | 4.6 |
| COMPARATIVE EXAMPLE 2 | 17 | $1.9 \times 10^{-5}$ | 4.8 |

As shown in Table 1, the organic semiconductor of Example 1 has higher solubility in 1 mL of chlorobenzene than those of the organic semiconductors of Comparative Examples 1 and 2, and hence it can be easily formed into a film by coating, etc., which finally leads to a reduction in the manufacturing cost of a device. Further, the organic semiconductor of Example 1 has higher hole mobility than those of the organic semiconductors of Comparative Examples 1 and 2, and hence it has been confirmed that it exhibits an excellent charge mobility characteristic. Furthermore, the organic semiconductor of Example 1 has a higher ionization potential than those of the organic semiconductors of Comparative Examples 1 and 2, and hence it has lower reactivity for an oxidation reaction, etc. Accordingly, the stability of the organic semiconductor of Example 1 is further improved in comparison with the organic semiconductors of Comparative Examples 1 and 2.

As described in the synthesis process of the organic semiconductor 1-1q to be used in Example 1, the organic semiconductor of Example 1 can be synthesized without using a transition metal, and hence the manufacturing cost can be suppressed.

The present invention should not be limited to the aforementioned embodiments, and various modifications, such as design modifications, can be made with respect to the embodiments based on the knowledge of those skilled in the art, and an embodiment with such a modification can be encompassed within the scope of the present invention.

The invention according to the aforementioned embodiments may be specified by following Items.

(Item 1) An organic semiconductor that is formed by a repeating unit having a structure represented by the following formula (1) and has an ionization potential higher than 5.0 eV.

[Formula 14]

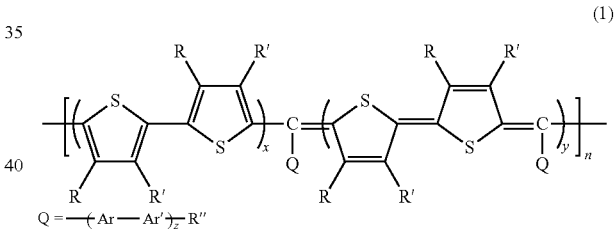

(1)

wherein Ar and Ar' are or are not the same as each other and each of them is independently a cyclic compound having a conjugated structure; R and R' are or are not the same as each other and each of them is independently one of a straight chain alkyl group, branched alkyl group, straight chain alkoxy group, branched alkoxy group, hydrogen, and halogen; R" is one of a straight chain alkyl group, branched alkyl group, straight chain alkoxy group, branched alkoxy group, hydrogen, and halogen; x, y, and z are multiples of 0.5, and x≤z, y≤z; and n is a constant of 1 to 1000.

(Item 2) The organic semiconductor according to Item 1, in which, in the formula (1), each of Ar and Ar' is an arylene group or hetero arylene group each having a substituent group.

(Item 3) The organic semiconductor according to Item 1, in which, in the formula (1), each of R and R' is one of a straight chain alkyl group, branched alkyl group, hydrogen, and halogen.

(Item 4) The organic semiconductor according to Item 1, in which, in the formula (1), R" is one of a straight chain alkoxy group, branched alkoxy group, and halogen.

(Item 5) The organic semiconductor according to Item 1, in which, in the formula (1), n is a constant of 5 to 1000.

(Item 6) The organic semiconductor according to any one of Items 1 to 5, in which, hole mobility of the organic semiconductor is $3.0\times10^{-5}$ cm$^2$/Vs or more, when measured by an SCLC method.

(Item 7) The organic semiconductor according to any one of Items 1 to 6, in which, solubility of the organic semiconductor is 25 mg or more in 1 mL of chlorobenzene.

Industrial Applicability

The present invention can be applied to organic electronic devices, such as, an organic thin-film solar cell, organic transistor, photosensor, and electroluminescense device.

What is claimed is:

1. An organic semiconductor that is formed by a repeating unit having a structure represented by the following formula (1) and has an ionization potential higher than 5.0 eV;

[Formula 1]

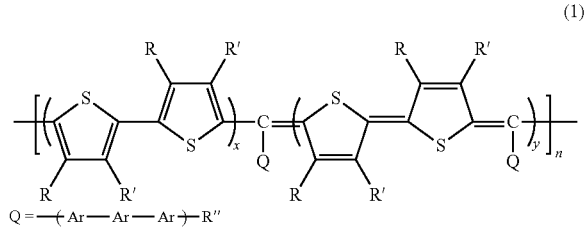

(1)

wherein Ar is independently a cyclic compound having a conjugated structure; R and R' are or are not the same as each other and each of them is independently one of a straight chain alkyl group, branched alkyl group, straight chain alkoxy group, branched alkoxy group, hydrogen, and halogen; R" is one of a straight chain alkyl group, branched alkyl group, straight chain alkoxy group, branched alkoxy group, hydrogen, and halogen; x=v=1; and n is a constant of 1 to 1000.

2. The organic semiconductor according to claim 1, wherein in the formula (1), is an arylene group or hetero arylene group each having a substituent group.

3. The organic semiconductor according to claim 1, wherein in the formula (1), each of R and R' is one of a straight chain alkyl group, branched alkyl group, hydrogen, and halogen.

4. The organic semiconductor according to claim 1, wherein in the formula (1), R" is one of a straight chain alkoxy group, branched alkoxy group, and halogen.

5. The organic semiconductor according to claim 1, wherein in the formula (1), n is a constant of 5 to 1000.

6. The organic semiconductor according to claim 1, wherein hole mobility of the organic semiconductor is $3.0\times10^{-5}$ cm$^2$/Vs or more.

7. The organic semiconductor according to claim 1, wherein, solubility of the organic semiconductor is 25 mg or more in 1 mL of chlorobenzene.

* * * * *